United States Patent [19]
Ferralli

[11] Patent Number: 4,629,030
[45] Date of Patent: Dec. 16, 1986

[54] PHASE COHERENT ACOUSTIC TRANSDUCER

[76] Inventor: Michael W. Ferralli, 10580 East Lake Rd., North East, Pa. 16428

[21] Appl. No.: 727,014
[22] Filed: Apr. 25, 1985
[51] Int. Cl.⁴ .............................................. H05K 5/00
[52] U.S. Cl. ................................... 181/155; 181/156; 181/175; 181/199
[58] Field of Search ................ 181/155, 156, 175, 199

[56] References Cited
U.S. PATENT DOCUMENTS 1,716,199  6/1929  Von Hoge et al. ................. 181/175
4,421,200 12/1983  Ferralli et al. .................... 181/155 X Primary Examiner—Benjamin R. Fuller

[57] ABSTRACT

An enclosure for a transduction element incorporates a geometrically shaped acoustically reflective shell. This acoustically reflective shell is shaped so that the inner surface thereof is at a least a section of that shape generated when an ellipse is rotated around a line which, lies in the plane of the ellipse, is oriented at any angle to the major axis of the ellipse, and contains one focus of the ellipse, or that shape generated when a continuum of ellipses having identical major axes are placed about a line which, lies in the plane of all the ellipses, is oriented at any angle with respect to the major axes of the ellipses, and contains a focal point common to all the ellipses. Such geometrically generated shapes will have one common focus and one distinct focal line. A transduction element placed about this focal line will, in operation, cause acoustic radiation to be focused and concentrated at a common focal point such that the common focus will act as a singular source of phase coherent acoustic radiation of any desired frequency independent beamwidth. Finally, by appropriate selection of transduction element and reflective shell composition, the device may operate as a transmitter of electromagnetic radiation.

14 Claims, 7 Drawing Figures

PHASE COHERENT ACOUSTIC TRANSDUCER

FIELD OF INVENTION

This invention relates to acoustic transducers and specifically to an improved wide dispersion acoustic transduction system.

DISCUSSION OF PRIOR ART

Heretofore, acoustic transducers have been designed which make use of a diaphragm which is electromagnetically or otherwise coupled to an electric signal in order to create a corresponding acoustic signal. Of these transducers, the compression driver is especially efficient in operation at high frequencies. The compression driver makes use of a large vibrating diaphragm which is confined to oscillate in a small volume containing a small exit from which the acoustic signal is emitted. With such confinement the action of the diaphragm is to compress the air within the volume such that the excursion of the air molecules from their equilibrium position at the exit is many times the excursion of the diaphragm from its equilibrium position. The amplitude of the acoustic wave thus produced is many times the amplitude of the mechanical wave of the diaphragm. An inherent limitation of the compression driver however results because the pathlengths of the acoustic compression wave from various points on to diaphragm to the exit are unequal. Thus waves produced in phase at the diaphragm surface will arrive at the exit without phase matching. The wavefront produced at the exit will therefore not be spatially coherent and the acoustic wave field produced by the compression driver will display interference phenomena. Further, the full efficiency of the compression driver will not be achieved due to the interference effects at the exit. Typically this deficiency is overcome by placing a phasing plug in the volume between the diaphragm and the exit. The intent of the phasing plug is to equalize pathlengths and thus eliminate phase incoherence. The phasing plug, however tends to dissipate the energy of the compression wave produced by the diaphragm and acoustically impede the diaphragm itself. Because of these actions the efficiency of the compression driver is greatly reduced. Many alternate designs of phasing plugs and compression drivers exist in the prior art but it appears to be an inherent quality of the phasing plug to reduce efficiency.

Another limitation of the current state of the art acoustic transducers is their frequency dependent beamwidth. The beamwidth of compression drivers as well as more conventional transducers is a function of both the size of the vibrating element (the transducer size in the case of conventional transducers and the exit dimension in the case of compression drivers) and the frequency of vibration. Compression drivers make use of an acoustic impedance matching device in the shape of a horn attached to the exit of the driver to partially control beamwidth as well as improve efficiency. This solution greatly improves efficiency but only partially resolves the beamwidth frequency dependence. Other compression drivers attempt to reduce this frequency dependence by resorting to very small compression driver exits, but this solution reduces transducer efficiency. Recently, a transducer system appeared in the state of the art which controls beamwidth dependence by use of an enclosure which is shaped as the envelope of ellipsoids have radially oriented distinct focal points as well as a common focal point. Transducers placed at the distinct focal points will have their acoustic radiation focused at the common focal point and, provided that the ellipsoids have essentially identical pathlengths from distinct focal point to ellipsoid to common focal point their acoustic energy will be coupled in phase. Further, the beamwidth of this device is wide and essentially frequency independent. The device, however, displays a radial interference pattern when the acoustic radiation of the transducers located on the radially distributed distinct focal points interacts. Specifically transducers on neighboring distinct focal points can destrucively interfere with each other causing radial diffraction or combing in the acoustic radiation field.

OBJECTS

Accordingly, an object of this invention is to provide a geometrically shaped enclosure for a diaphragm such that all acoustic pathlengths from the diaphragm surface to the enclosure exit are substantially identical. Another object of this invention is to provide a geometrically shaped enclosure which will focus acoustic waves produced by the diaphragm at a point coincident with the exit of the enclosure. Another object of the invention is to increase the beamwidth of the acousitc wave emitted from the exit and provide for the relative consistency of the beamwidth as a function of acoustic wave frequency.

Still another object of this invention is to increase the efficiency of transduction of energy by eliminating the need for a phasing plug. It is another object of the invention to provide a single enclosure containing a large diaphragm or a nonradially interfering array of transducers which will appear to act as a single source with wide and essentially frequency invariant beamwidth.

It is another object of the invention to create an exit of focused acoustic radiation which will generate a beam shape controlled by a geometrically shape enclosure. It is still another object of this invention to create an acoustic transduction system which will display a nonradially interfering acoustic field.

It is an object of this invention to produce a transduction system which can be used to transduce acoustic energy into electrical energy with both stereo and monaural compatability.

DRAWINGS

FIG. 3a is a section on line 1—1 of FIG. 3.

DESCRIPTION

Figure 1:
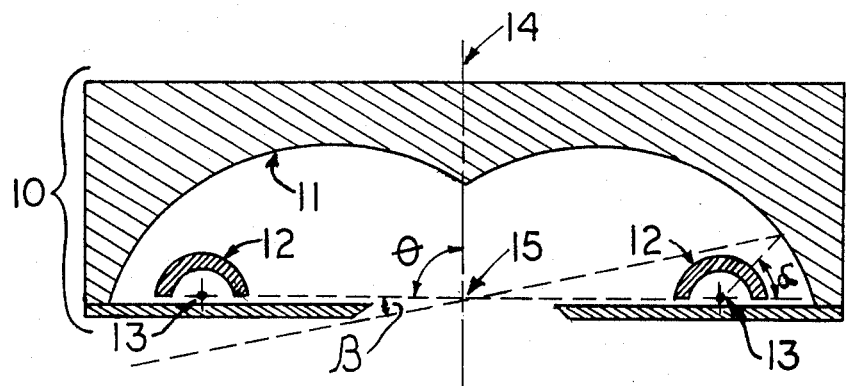
FIG. 1 is a full section on line 1—1 of FIG. 2 as viewed from the top of one embodiment of the invention utilizing a shell whose shape is that generated when an ellipse is rotated around a line which lies in the plane of the ellipse, is oriented at an angle $\phi$ to the major axis of said ellipse and contains one of the focal points thereof.
Figure 2:
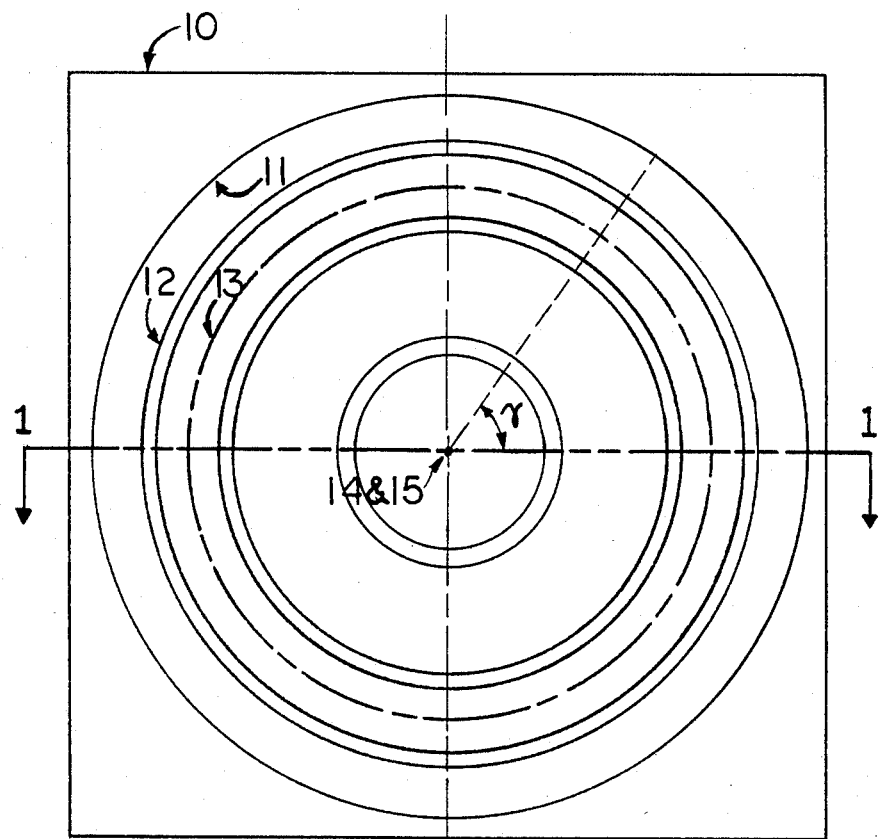
FIG. 2 is a front view thereof.

FIGS. 1 and 2 of the drawings illustrate the top and front views of an enclosure designed to radiate acoustic energy from a daiphragm placed therein. The enclosure 10 incorporates a geometrically shaped shell 11 and contains a diaphragm 12 shaped as a section of a torus which is located so as to be centered about the line 13 containing the distinct focal points of elliptically shaped cross section of the shell 11. Suitable materials for the shell 11 include wood, metal, reinforced resin, or other structural material. The diaphragm 12 may be made of plastic, metal, resin impregnated cloth, or other suitable material. The dimensions of the device may vary in order to suit the desired end use, but it is to be understood in all cases that for most efficient operation the dimensions of the enclosure should be larger than the longest wavelength of acoustic radiation produced by the transducer. The shell 11 is shaped substantially as that figure generated when an ellipse is rotated about a line 14 lying in the plane of the ellipse, oriented at an angle $\phi$ with the major axes of the ellipse, and containing the common focal point 15. The angle $\phi$ is chosen according to the desired ability of the enclosure to intensify and radiate acoustic energy and may be varied as a function of rotation about the line 14.

Figure 3B:
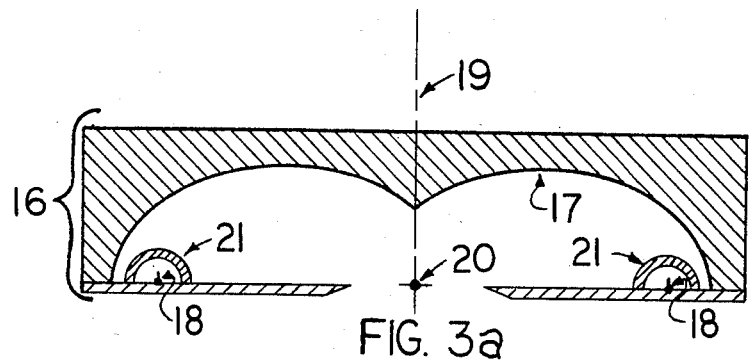
FIG. 3b is a section on line 2—2 of FIG. 3.
Figure 3:
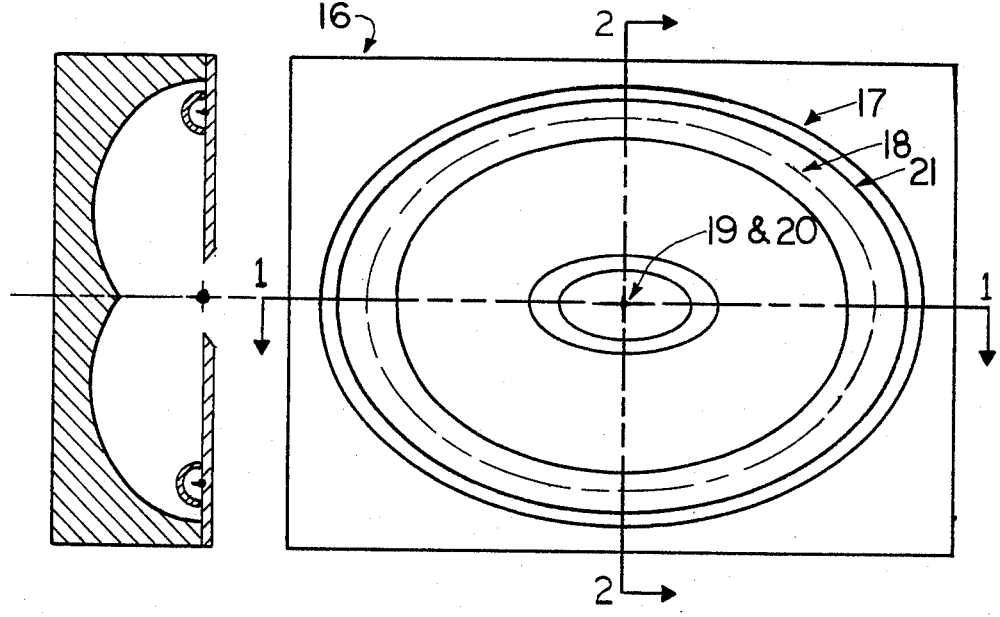
FIG. 3 illustrates another embodiment of the invention utilizing a shell whose shape is generated when a continuum of ellipses having identical lengths of major axes are placed radially around a line which is contained by all the ellipses and oriented at an angle $\phi$ to all such radially distributed major axes and which contains a focal point common to all said ellipses.

FIGS. 3, 3a, and 3b of the drawings illustrate three views of another enclosure designed to radiate acoustic energy from a diaphragm placed therein. FIG. 3a is a section on line 1—1 of FIG. 3 and FIG. 3b is a section on line 2—2 of FIG. 3. The enclosure 16 incorporates a geometrically shaped shell 17 and incorporates a diaphragm 21 shaped as a section of a tube centered about a line 18 containing the distinct focal points of the elliptically shaped crossection of the shell 17. The shell 17 is shaped substantially as the figure generated when a continuum of ellipses having identical lengths of major axes but different focal lengths are placed radially around a line 19 which lies in the plane of said ellipses, is oriented at an angle $\phi$ to all such radially distributed major axes and which contains a focal point 20 common to all said ellipses. The angle $\phi$ is chosen according to the desired ability of the enclosure to intensify and radiate acoustic energy and may be varied as a function of rotation about line 19. Further the focal lengths of the ellipses radially distributed about line 19 may be varied as desired so long as the major axes of said ellipses remain identical. Suitable material for the shell 17 include wood, metal, reinforced resin, or other structural material with reasonable acoustic reflection characteristics. The diaphragm 21 may be made of plastic, metal, resin impregnated cloth, or other suitable material.

Figure 4:
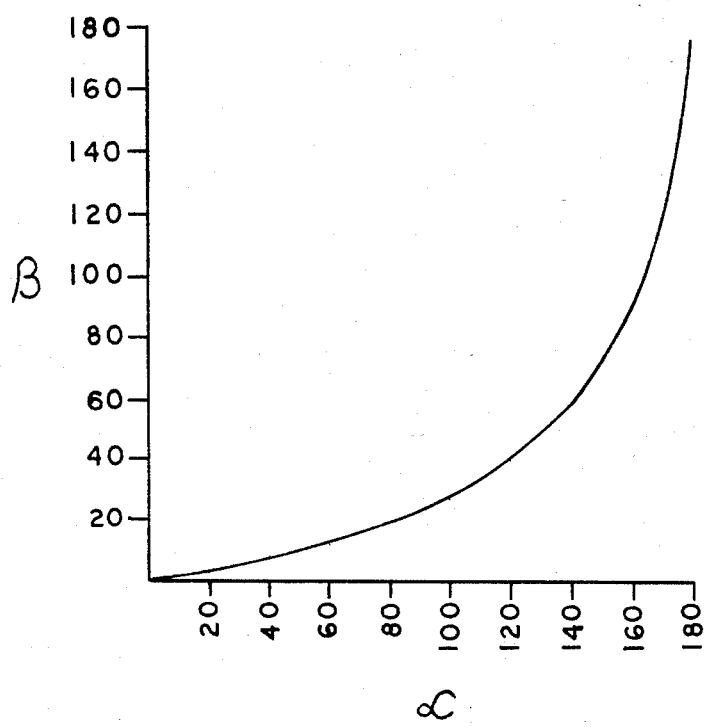
FIG. 4 is a plot of the functional relationship between $\alpha$, the angle of acoustic radiation emitted from the diaphragm in the invention and $\beta$, the corresponding angle of acoustic radiation emitted from the common focal point.

FIG. 4 of the drawing shows the relationship between the angle of radiation emitted from a diaphragm contained within the enclosure of the invention and the corresponding angle of acoustic radiation emitted from the exit of the invention.

Figure 5:
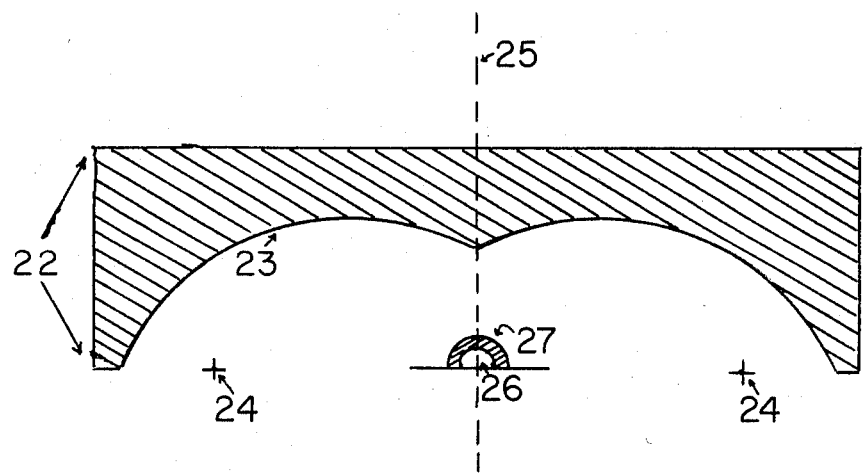
FIG. 5 illustrates another embodiment of the invention using a shell whose shape is identical to that illustrated in FIGS. 1 and 2 or FIG. 3, but wherein the transducer is placed at the focal point common to all the ellipses.

FIG. 5 of the drawings illustrates a view of another enclosure designed to radiate energy from a transducer placed therein. The enclosure 22 incorporates a geometrically shaped shell 23 and a transducer 27 centered about a line 25 which contains the common focal point of the elliptically shaped crossection of the shell 23. The shell 23 may be shaped in a manner identical to shell 11 of FIGS. 1 and 2 or identical to shell 17 of FIG. 3 and may be made of the same materials.

OPERATION

In the operation of the enclosure 10, acoustic radiation from the diaphragm 12 is directed substantially toward the interior of the acoustically reflective shell 11. The Diaphragm 12 acts as a transducer element and converts an electrical signal to an acoustical signal by any methods known in the state of the art such as by electromagnetic or piezoelectric means. The diaphragm 12 is at least approximately centered about the line 13 such that the acoustic signal produced by it appears to have as an approximate source the focal line 13. The acoustic signal produced by diahragm 12 will thus be reflected from shell 11 and concentrated and focused in the region of the common focal point 15. The shell 11, being elliptically shaped as hereinbefore described will cause all acoustic radiation from diaphragm 12 to travel the same distance in reaching the fcal point 15 and thus all acoustic radiation arriving at focal point 15 will arrive in phase so long as all points on diaphragm 12 produce phase matched acoustic radiation. Under the above conditions, focal point 15 will appear to be the source of acoustic radiation rather than the actual transducing diaphragm 12 itself. Further, acoustic radiation emanating from focal point 15 will be in phase and have intensity and phase consistency above that produced by any other arrangement of diaphragm 12 not involving a shell shaped such as shell 11. The beam width angle $\beta$ of the acoustic radiation from focal point 15 is related to the angle $\alpha$ of acoustic radiation emanating from the diaphragm 12 by the equation $$\sin \alpha/F + A \cos \alpha = \sin \beta/A \cos \beta - F$$

where F is the focal length of the ellipse and A is the length of the major axis of the ellipse. Thus the beamwidth angle $\beta$ is related to acoustic radiation angle $\alpha$ as shown in FIG. 4. It should be noted from FIG. 4 that for small angles of $\alpha$, a large change in $\alpha$ results in a small change in $\beta$. Thus the beamwidth of the acoustic radiation emanating from the common focal point 15, being determined by the angular intensity distrubution from the diaphragm 12 at small angles of $\alpha$, will be largely insensitive of corresponding changes in the beamwidth of the acoustic radiation emanating from the diaphragm 12. Thus, the beam width of the radiation emanating from the common focal point will be insensitive to the beam width of the acoustic radiation emanating from the diaphragm 12. It is well known that the beamwidth of acoustic radiation emanating from diaphragms tends to decrease with increasing frequency of the radiation, but because of the nonlinear redistribution of acoustic energy by the elliptical shape of the shell 11, the frequency dependence of the beamwidth emanating from the common focal point 15 will be minimal. The embodiment of the invention illustrated in FIGS. 1 and 2 will thus act to produce an acoustic radiation pattern whose beamwidth is essentially frequency independent and much larger than corresponding beamwidth of other transducers. Since all acoustic radiation emanating from the diaphragm 12 arrives at the common focal point in phase, no phasing plug is needed and the efficiency of the invention is much improved when compared to other transducers. The beam width of the acoustic radiation emanating from the common focal point 15 can be made larger or smaller than the beamwidth of the acoustic radiation emanating from the diaphragm 12 by suitable choice of the length of the major and minor axes of of the ellipse used to generate the shell 11 and by choice of angle $\phi$ between the line 14 and the ellipse major axis. Also the beamwidth as function of angle $\gamma$ as illustrated in FIG. 2 can be varied by appropriately varying angle $\phi$ as a function of angle $\gamma$.

The embodiment of the invention illustrated in FIG. 3 operates in a manner similar to that illustrated in FIGS. 1 and 2 except that, owing the shell being generated by a continuum of ellipses having identical lengths of major axes, the line 18 containing the distinct focal points may not describe a circle. However, since the ellipses all have identical major axis lengths, the pathlengths traveled by acoustic radiation emanating, or appearing to be emanating, from the distinct focal line 18 to the shell 17 and, upon reflection, to the common focal point 20 will be identical. However the beamwidth of the acoustic radiation emanating from the common focal point 20 is a function of the shape of a corresponding section of shell 17 and thus suitable choice the corresponding section of shell 17 will result in a resultant beamwidth. It is thus obvious that the beamwidth can be altered as a function of $\gamma$ by appropriate selection of ellipses used in forming the shell, that selection being constrained by the provision that all said ellipses have identical major axes. Thus the embodiment of the invention illustrated in FIG. 3 provides for an additional dimension in the control of the shape of the beamwidth of acoustic radiation emanating from the common focal point 20.

The embodiment of the invention illustrated in FIG. 5 operates in a manner similar to that illustrated in FIGS. 1 and 2 or FIG. 3, except that the transducer 27 is placed at the common focal point 26 rather than about the distinct focal points 24. Acoustic radiation emanating from the transducer 27 will be reflected from shell 23 and concentrated and focused in the region of the distinct focal points 24. The shell 23, being elliptically shaped as hereinbefore described, will cause all acoustic radiation from the transducer 27 to travel the same distance in reaching the distinct focal points 24 and thus all radiation arriving at the distinct focal points 24 will be in phase. Thus the distinct focal points 24 will appear to be the source of radiation rather than the actual transducer 27. Just as in the embodiments of the invention illustrated in FIGS. 1 and 2 or FIG. 3 the beam width of the radiation emanating from the distinct focal points may be controlled by suitable choice of the length of the major and minor axes of the ellipses used to generate the shell 23 as well as the portion of the shell utilized.

It is to be understood that, although the diaphragm illustrated in the above embodiments of the invention is shown as a continuous element, it could be a segmented series of elements which could be operated in phase with one another to generate acoustical energy or with differences in phase and/or intensity to cause a desired effect in the resultant beam from the common focal point.

It is also to be understood that precise location of each of the components of the invention is not necessary for its operation due to the relatively long wavelengths associated with acoustic radiation. Tolerances in construction of the invention including the location of all elements thereof should not, in general, exceed $\frac{1}{4}$ of the wavelength of the highest frequency of acoustic radiation for which the invention is to be used. It is also understood that the diaphragm in the embodiments of the invention need to be located near or about the line containing the distinct focal points to the extent that radiation produced or received by said diaphragm travels approximately the same pathlength from the common focal point to the diaphragm, that is, to within $\frac{1}{4}$ of the wavelength of the highest frequency of radiation for which the invention is expected to be functional. It is also to be understood that the invention would operate equally well as a transducer of electromagnetic radiation so long as the electromagnetic radiation wavelength is not smaller that the tolerances to which the invention could be constructed and the electromagnetic radiation contained an identifiable phase.

While the above description contains many specifities, these should not be construed as limitations on the scope of the invention, but rather as an exemplification of a number of preferred embodiments thereof. For example the invention could be used to concentrate ultrasonic acoustic energy onto a kidney stone or other undesirable deposit in a patient and provide a means for pulverizing said stone or deposit without surgical intervention. In this embodiment the kidney stone or deposit would be located at the position of the common focal point while the diaphragm would be used as a generator of ultrasonic acoustic energy. Said energy being concentrated and phase matched at the common focal point would be sufficient to cause pulverization of the kidney stone or deposit without damage to surrounding tissue. Accordingly, the scope of this invention should be determined not by the embodiments illustrated, but by the appended claims and their legal equivalents.

What is claimed is:

1. An enclosure which comprises an acoustically reflective shell wherein said shell comprises at least a section that forms an elliptical structure that generates a continuum of ellipses when rotated about a straight line which lies in a plane of the elliptical structure, contains one focal point of the elliptical structure, and is oriented at any finite angle $\phi$ to the major axis of the elliptical structure, such that the resultant surface is that of a continuum of elliptical structures rotated about a focal point common to all the elliptical structures, but above said surface, being referred to as the common focal point, and such that the other focal points of the elliptical structure, being distinct from one another, form a curve, said curve being referred to as a distinct focal curve, and such that a single acoustic transducer may be located about this distinct focal curve so that acoustic radiation produced therefrom travels the same pathlength from said transducer to the acoustically reflective shell and thence to the common focal point, and such that acoustical radiation emanating from said transducer, being in phase, arrives at the common focal point in phase.

2. An enclosure according to claim 1 wherein the acoustic transducer is a acoustic radiation generator.

3. An enclosure according to claim 1 wherein the angle $\phi$ between the ellipse major axis and the line lying in the plane of the ellipse and containing the common focal point is varied as the said ellipse is rotated about said line.

4. An enclosure according to claim 1 wherin the acoustically reflective shell is reflective of electromagnetic radiation of wavelength larger than the tolerance to which the reflective shell may be made and wherein the transducer is an electromagnetic rather than acoustic transducer.

5. An enclosure according to claim 1 wherein the the transduction element consists of a number of segments, which may be separate transducers, and which may independently transduce acoustic energy.

6. An enclosure according to claim 1 wherein a kidney stone or other undesirable deposit is positioned substantially at the said common focal point and is disintegrated by said waves.

7. An enclosure according to claim 1 wherein the transducer may be placed at the common focal point so that acoustic radiation produced therefrom travels the same pathlength from said transducer to the acoustically reflective shell and thence to the distinct focal curve, and such that acoustic radiation emanating from said transducer, being in phase arrives at the distinct focal curve in phase.

8. An enclosure which comprises an acoustically reflective shell wherein said shell comprises at least a section that forms an elliptical structure that generates a continuum of ellipses when a continuum of said elliptical structures are positioned radially about a straight line which lies in a plane of all the elliptical structures, contains one focal point common to all the elliptical structures, and is oriented at any finite angle $\phi$ with respect to the major axes of the elliptical structures, such that all said elliptical structures have identical lengths of major axes and are radially placed so that said straght line contains a focal point common to all the ellipses, but above said acoustically reflective shell, being referred to as the common focal point, and such that the other focal points of the continuum of elliptical structures form a curve, said curve being referred to as the distinct focal curve, and such that an acoustic transducer may be located about this distinct focal curve so that acoustic radiation produced therefrom travels the same pathlength from said transducer to the acoustically reflective shell and thence to the common focal point, and such that the acoustical radiation emanating from the transducer, being in phase, arrives at the common focal point in phase.

9. An enclosure according to claim 8 wherein the acoustic transducer is an acoustic radiation generator.

10. An enclosure according to claim 8 wherein the angle $\phi$ between the major axes of the continuum of ellipses and the line lying in the plane of the continuum of ellipses and containing the common focal point is varied about said line.

11. An enclosure according to claim 8 wherein the acoustically reflective shell is reflective of electromagnetic radiation of wavelength larger than the tolerance to which the reflective shell may be made and wherein the transducer is an electromagnetic rather than acoustic transducer.

12. An enclosure according to claim 8 wherein the transduction element consists of a number of segments, which may be separate transducers, and which may independently transduce acoustic energy.

13. An enclosure according to claim 8 wherein a kidney stone or other undesirable deposit is positioned substantially at the said common focal point and is disintegrated by said waves.

14. An enclosure according to claim 8 wherein the transducer may be placed at the common focal point so that acoustic radiation produced therefrom travels the same pathlength from said transducer to the acoustically reflective shell and thence to the distinct focal curve, and such that acoustic radiation emanating from said transducer, being in phase arrives at the distinct focal curve in phase.

* * * * *